United States Patent [19]

Kees, Jr.

[11] Patent Number: 4,681,107
[45] Date of Patent: Jul. 21, 1987

[54] DEVICE FOR HOLDING AN ANEURYSM CLIP

[75] Inventor: George Kees, Jr., Alexandria, Ky.

[73] Assignee: Kees Surgical Specialty Co., Wilder, Ky.

[21] Appl. No.: 815,388

[22] Filed: Dec. 31, 1985

[51] Int. Cl.$^4$ .............................................. A61B 17/12
[52] U.S. Cl. .................................. 128/325; 29/243.56
[58] Field of Search ....................... 128/325, 303, 346; 29/243.36

[56] References Cited

U.S. PATENT DOCUMENTS

| | | | |
|---|---|---|---|
| 4,291,734 | 12/1980 | Kandel et al. | 128/325 |
| 4,367,746 | 1/1983 | Derechinsky | 128/325 |
| 4,509,517 | 4/1985 | Zibelin | 128/348 |

Primary Examiner—Stephen C. Pellegrino
Attorney, Agent, or Firm—James W. Pearce; Roy F. Schaeperklaus

[57] ABSTRACT

A holder for an aneurysm clip. A clip holding tool can be drawn into a tubular clip opening fitting. The clip holding tool has arms engageable with the aneurysm clip to hold the aneurysm clip. Portions of the arms are engageable with the interior of the clip opening fitting to cause the arms of the clip holding tool to close to clip holding position when the clip holding tool is drawn into the tubular clip opening fitting. A mouth defining surface of the clip opening fitting engages the aneurysm clip for causing opening of the aneurysm clip as the clip holding tool is advanced along the clip opening fitting.

5 Claims, 11 Drawing Figures

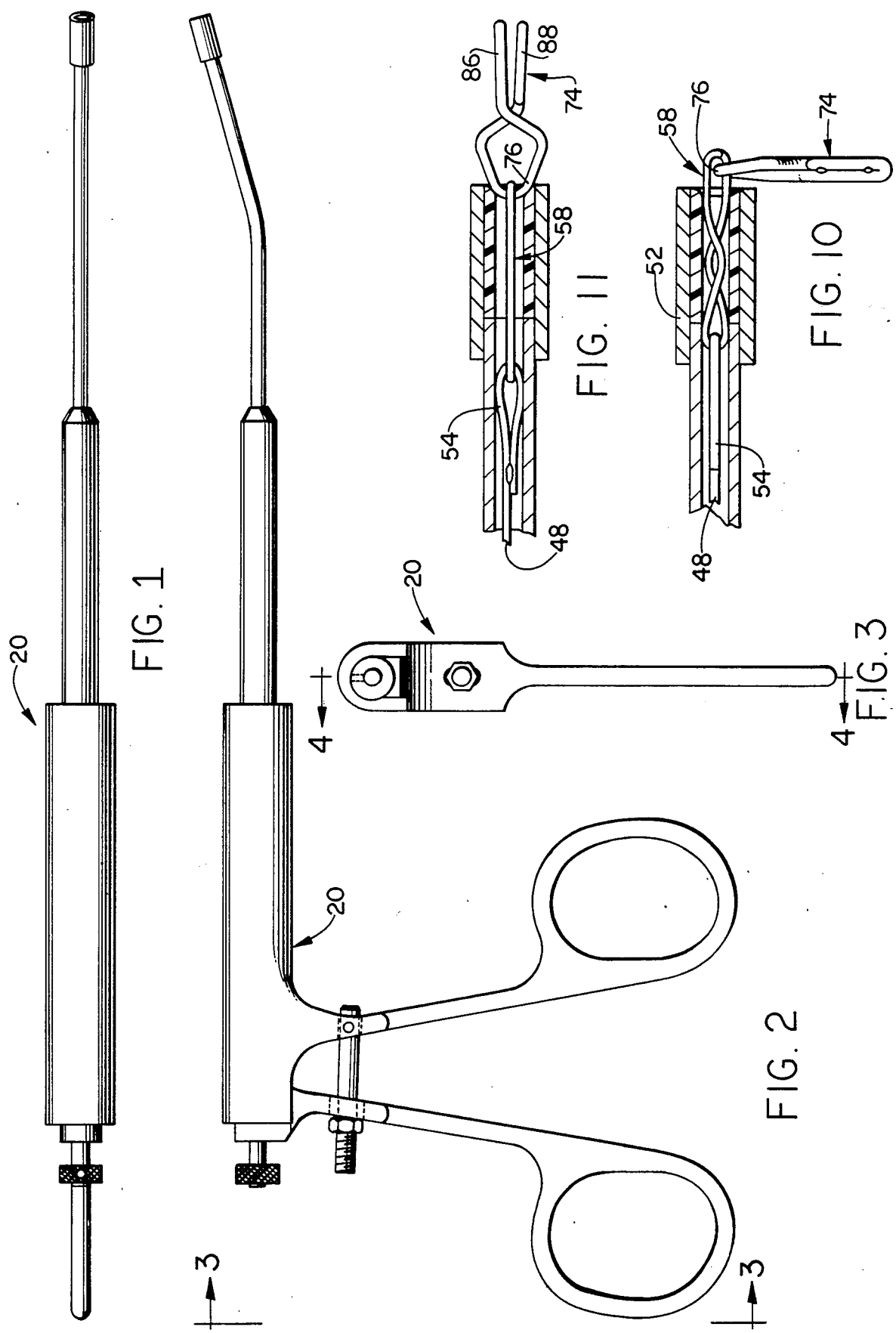

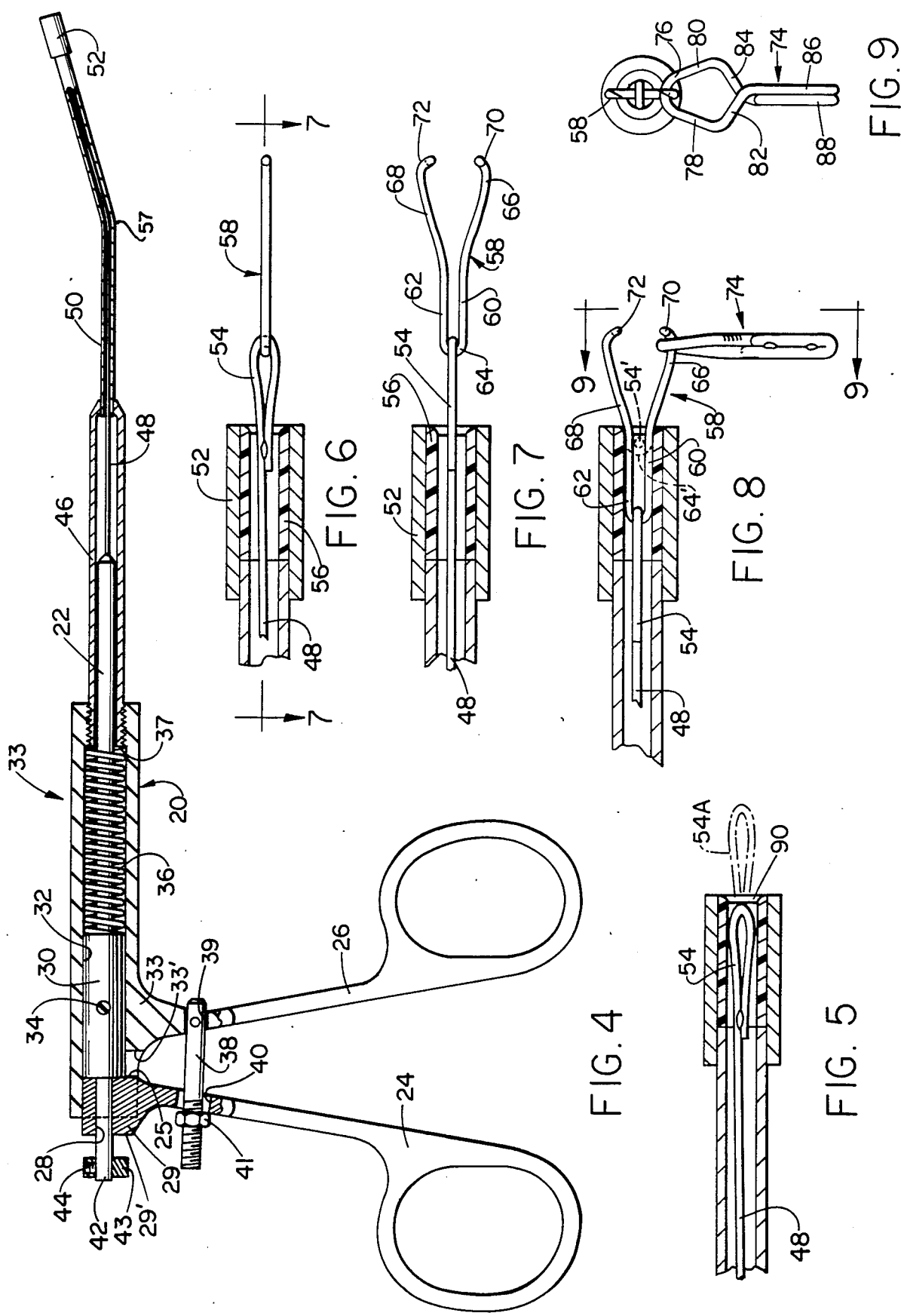

DEVICE FOR HOLDING AN ANEURYSM CLIP

BACKGROUND OF THE INVENTION

This invention relates to a device for holding an aneurysm clip in open condition as the aneurysm clip is positioned and then applied by releasing the clip to close upon an aneurysm in selected position.

An object of this invention is to provide a clip holder which holds an aneurysm clip in open position until actuated to release opening pressure on the aneurysm clip and to permit closing and release of the aneurysm clip.

SUMMARY OF THE INVENTION

Briefly, this invention provides a clip holder which includes a tubular clip opening fitting into and through which a clip holding tool is drawn. As the clip holding tool is drawn into and along the tubular clip opening fitting, the clip holding tool can engage sides of the tubular clip opening fitting and is closed to hold the aneurysm clip. As the clip holding tool is drawn further into the tubular clip opening fitting, the aneurysm clip engages the mouth of the tubular clip opening fitting and jaws of the aneurysm clip are caused to open. A spring holds the clip holding tool in clip open position. The clip holding tool can be returned along the tubular clip holding fitting to first cause release of pressure on the aneurysm clip to permit the aneurysm clip to close. Further advance of the clip holding tool in returning direction permits the clip holding tool to open to release the aneurysm clip.

The above and other objects and features of the invention will be apparent to those skilled in the art to which this invention pertains from the following detailed description and the drawings, in which:

BRIEF DESCRIPTION OF THE DRAWINGS

FIG. 1 is a top plan view of a device for holding an aneurysm clip which is constructed in accordance with an embodiment of this invention;

FIG. 2 is a view in side elevation of the clip holding device shown in FIG. 1;

FIG. 3 is a view in end elevation of the clip holding device taken in the direction indicated by arrows 3—3 in FIG. 2;

FIG. 4 is a view generally in section taken on the line 4—4 in FIG. 3;

FIG. 5 is a fragmentary view on an enlarged scale in upright section of an end portion of the device showing a flexible wire in partly retracted position in full lines and in extended position in dot-dash lines;

FIG. 6 is a fragmentary view in section of the end portion similar to FIG. 5 with the flexible wire or cable in extended position and with a clip holding tool mounted thereon;

FIG. 7 is a fragmentary view in section taken on the line 7—7 in FIG. 6;

FIG. 8 is a fragmentary view in section of the end portion with the clip cable and the clip holding tool in partly retracted positions, an aneurysm clip being shown in association therewith;

FIG. 9 is a view in end elevation looking in the direction of the arrows 9—9 in FIG. 8;

FIG. 10 is a fragmentary view in section of the end portion showing the cable further retracted and with a major portion of the clip holding tool inside a clip opening fitting, the clip holding tool being shown in closed position; and FIG. 11 is a fragmentary view in section of the end portion showing the clip holding tool in further retracted position, the aneurysm clip being shown in open position.

In the following detailed description and the drawings, like reference characters indicate like parts.

DESCRIPTION OF THE PRESENTLY PREFERRED EMBODIMENT

In FIGS. 1–4 inclusive is shown a device 20 for holding, opening and applying an aneurysm clip, which is constructed in accordance with an embodiment of this invention. The device 20 includes an elongated rod 22, a first handle portion 24, and a second handle portion 26. The handle portions 24 and 26 are slideably mounted on the rod 22. The rod 22 extends through a bore 28 in a head 29 of the first handle portion 24. An elongated collar 30 mounted on the rod 22 is slideable in a counterbore 32 in a head 33 of the second handle portion 26. The collar 30 is attached to the rod 22 by a set screw 34. A compression spring 36 is mounted on the rod 22 and bears on the collar 30 and on a shoulder 37 at one end of the counterbore 32 to urge the rod 22 to the left as shown in FIG. 4. The collar 30 can engage the head 29 of the first handle portion 24. A tension rod 38 limits advance of the rod 22. One end portion of the tension rod 38 is secured in a transverse bore 39 in the second handle portion 26. An opposed end portion of the tension rod 38 extends through a slot 40 in the first handle portion 24 and is threaded to receive a nut 41, which bears on the first handle portion 24 to adjustably limit the movement of the rod 22 under the influence of the spring 36. The rod 22 can be moved to the right as shown in FIG. 1 by advance of the first handle portion 24 or by pressure on an exposed end portion 42 of the rod 22. A stop collar 43 is mounted on the rod 22 and held in position thereon by a set screw 44. The stop collar 43 limits movement of the rod 22 to the right as shown in FIG. 4.

A first extension tube 46 is mounted on the second handle portion 26 at the shoulder 37. An end portion of the rod 22 reciprocates inside the first extension tube 46. A flexible wire 48 is attached to the rod 22. A second extension tube 50, which as shown may have a bend 57 in its mid-section, is attached to the first extension tube 46, and the flexible wire 48 moves inside the second extension tube 50. At a free end of the second extension tube 50 is mounted a tubular clip opening fitting 52. A free end of the flexible wire 48 forms a loop or eye 54 which can move inside the tubular clip opening fitting 52. A lining portion 56 of the tubular clip opening fitting 52 can be formed of the plastic material commonly called Teflon (a trademark of E. I. duPont de Nemours and Co.). An obtuse angle bend 57 formed in the second extension tube 50 permits turning of the tubular clip opening fitting 52 of device 20 to readily effect oblique orientation of an aneurysm clip held in relation to fitting 52.

When the collar 43 is removed from the rod 22, the rod 22 can be advanced to the position at which the loop 54 of the flexible wire 48 is shown in FIGS. 6 and 7 and in dot-dash lines at 54A in FIG. 5. Then, a clip holding fitting 58 can be mounted on the loop 54. The clip holding fitting 58 is formed of spring metal and includes arms 60 and 62 connected by a central bend section 64. The arms 60, 62 of the clip holding fitting 58 include respective connecting portions 66 and 68 spaced from bend section 64 and, in unstressed condition as shown in FIG. 7, connecting portions 66,68 normally diverge as they extend away from the central bend section 64 to terminal end portions 70 and 72, which are normally directed toward each other and have beveled end faces which overlap when the fitting 58 is closed to hold a clip 74. An aneurysm clip 74 can be held and supported by the clip holding fitting 58.

The aneurysm clip 74 (FIG. 9) can be of the type which includes a central bend spring portion 76, diverging first connecting portions 78 and 80 integrally formed with end portions of the central bend spring portion 76, crossing converging second connecting portions 82 and 84 integrally formed with the first connecting portions 78 and 80, and jaw members 86 and 88 integrally formed with the second connecting portions 82 and 84, respectively. This type of aneurysm clip is shown and claimed in my co-pending applications Ser. No. 06/815,231 filed Dec. 31, 1985 and Ser. No. 06/815,247 filed Dec. 31, 1985.

When the loop 54 is drawn inwardly of the tubular clip opening fitting 52 to the position shown in FIGS. 8 and 9, sides of the arms 60 and 62 engage the lining portion 56 of the tubular clip opening fitting 52, and the connecting portions 66,68 with terminal end portions 70,72 are open to receive a clip 74. As loop 54 is drawn further inwardly from the FIGS. 8 and 9 position toward the position shown in FIG. 10, sides of connecting portions 66,68 and terminal end portions 70,72 are urged together to close on and hold the aneurysm clip 74.

To preclude disengagement of clip holding fitting 58 from loop 54, the collar 43 can, by tightening set screw 44, be secured in fixed relation on rod 22 so collar 43 will be in abutment with face 29' of the heel of first handle portion 24 when the forward face 25 of the latter is in abutment with stop face 33' when loop 54 is in the position 54' shown in dot-dash lines in FIG. 8. In the latter position, loop 54 retains central bend section 64 of clip holding fitting 58 and adjacent portions of arm portions 60, 62 in the bore of lining 56 of the tubular clip opening fitting 52.

However, in normal use, it is desirable that the clip holding fitting 58 be advanceable between the clip loading and unloading position shown in full lines in FIGS. 8 and 9, and the clip applying position shown in FIG. 11 in which the clip is held in open position ready for application to an aneurysm. The movement of the clip holding fitting 58 between those normal operating limit positions is effected by moving first handle portion 24 toward and away from second handle portion 26; that is, when handle portion 24 as viewed in FIG. 4 is moved toward handle portion 26 to bring its forward face 25 into abutment with opposed stop face 33' of the handle 26, the clip holding fitting 58 is advanced from the FIG. 11 position to the full line position in FIG. 8 wherein clip 74 may be loaded (or unloaded). Upon relaxing of the force urging first handle portion 24 toward second handle portion 26, compression spring 36 advances the first handle portion 24 away from second handle portion 26, and, loop 54 concurrently progressively draws clip holding fitting 58 into the bore in the lining 56 of clip opening fitting 52 thereby successively closing the clip holding fitting 58 to closed condition with terminal end portions 70,72 in overlapping abutment and drawing fitting 58 further into the tubular clip opening fitting 52 to draw the aneurysm clip 74 into cooperation with the clip opening fitting 52 to apply compressive forces to the aneurysm clip 74 to effect desired opening of the jaws of aneurysm clip 74.

When the flexible wire 48 is advanced from the position shown in FIG. 10 to that shown in FIG. 11, the central bend spring portion 76 of the aneurysm clip 74 is drawn into a mouth 90 of the liner portion 56 of the tubular clip opening fitting 52. The mouth 90 has an inner wall section which is frusto-conic in inner shape as shown in FIG. 5. The diverging first connecting portions 78 and 80 of the aneurysm clip 74 engage the frusto-conic mouth 90 to cause opening of the jaws 86 and 88 of aneurysm clip 74 as shown in FIG. 11. The spring 36 (FIG. 4) impresses a sufficient tension on the flexible wire 48 and the rod 22 to hold the jaws 86 and 88 of the aneurysm clip 74 in open position.

The magnitude of the separation or opening of the jaws 86,88 of a particular aneurysm clip; viz., clip 74, effected by expansion of spring 36 is determined by the limitation of movement of first handle portion 24 away from second handle portion 26 into engagement with nut 41 on tension rod 38. The magnitude of the opening of jaws 86,88 shown in FIG. 11 corresponds to the relative positions of first and second handle portions 24,26 when the former is abutting nut 41 as shown in FIG. 4. Movement of nut 41 leftward from the position in which it is shown in FIG. 4 would result in opening of jaws 86,88 wider than they are shown in FIG. 11, while rightward movement of nut 41 from the FIG. 4 position would result in the jaws 86,88 being closer together than as shown in FIG. 11. The rod 22 and flexible wire 48 are joined together so that they rotate in unison. Further, the loop 54 associated with clip holding fitting 58 as shown in FIGS. 8, 9, 10 and 11 results in fitting 58 rotating substantially in unison with rod 22, wire 48 and loop 54 once any slight amount of rotational play as may exist between loop 54 and fitting 58 has been taken up. Thus, aneurysm clip 74 in the position depicted in FIG. 11 may be rotated relative to tubular clip opening fitting 52 which is mounted in fixed relation on second extension tube 50 which in turn is in fixed relation to tube 46 and second handle portion 26. Thus, a surgeon holding the device 20 by handles 24,26 in one hand may rotate or otherwise position the device 20 to support the aneurysm clip 74 so its jaws are in the alignment desired for its application to an aneurysm, and may with a second hand rotate stop collar 43, which is in fixed relation on rod 22, to effect rotation of clip 74 on the axis of tubular clip opening fitting 52. Thus, while repositioning of device 20 into a desired position of jaw alignment can effect rotation of clip 74 into an undesirable position rotationwise, the additional control of rotational positioning of that clip is provided by collar 43 to further position the aneurysm clip as desired. When the jaws 86,88 of the clip are properly positioned for jaw alignment as desired and rotated to position them on opposite sides of the neck of an aneurysm, advancing of first handle portion 24 toward second handle portion 26 effects compression of spring 36 and progressive closing of jaws 86,88 of the aneurysm clip on the neck of an aneurysm to close the latter and then opens clip holding fitting 58 so that it may be disengaged from the placed aneurysm clip in order that the device 20 may be withdrawn from the site of application of the clip.

The clip applying tool illustrated in the drawings and described above is subject to structural modification without departing from the spirit and scope of the appended claims.

Having described my invention, what I claim as new and desire to secure by Letters Patent is:

1. A holder for an aneurysm clip which comprises a tubular clip opening fitting, a clip holding tool, means for drawing the clip holding tool through the tubular clip opening fitting, the clip holding tool having arms engageable with the aneurysm clip to hold the aneurysm clip, portions of the arms being engageable with the clip opening fitting to cause the arms of the clip holding tool to close to clip holding position when the clip holding tool is drawn into the tubular clip opening fitting, means on the tubular clip opening fitting engageable with the aneurysm clip for causing opening of the aneurysm clip in correlation to advance of the clip holding tool along the tubular clip opening fitting and adjustable stop means for selecting the limit of advance of the clip holding tool along the clip opening fitting as corresponds to the desired opening of a selected aneurysm clip held by the clip holding tool, whereby the holder may be adapted to hold a selected aneurysm clip in a pre-selected open attitude.

2. A holder as in claim 1 in which the means on the tubular clip opening fitting engageable with the aneurysm clip includes a mouth defining surface on the tubular clip opening fitting and the aneurysm clip includes arms engageable with the mouth defining surface of the tubular clip opening fitting to cause opening of the aneurysm clip.

3. A holder for an aneurysm clip which comprises rod means, a first handle means and a second handle means slideably mounted on the rod means, spring means bearing on the rod means and on the second handle means to urge the rod means lengthwise of the second handle means, means on the rod means for bearing on the first handle means to urge the first handle means lengthwise of the second handle means so that the spring means can urge the first handle means lengthwise of the second handle means, guide tube means mounted on the second handle means, tension link means mounted on the rod means and movable lengthwise of the guide tube means, a tubular clip opening fitting mounted on the guide tube means, a clip holding tool, means connecting the clip holding tool to the tension link means, movement of the tension link means drawing the clip holding tool through the tubular clip opening fitting, the clip holding tool having arms engageable with the aneurysm clip to hold the aneurysm clip, portions of the arms beng engageable with the interior of the clip opening fitting to cause the arms of the clip holding tool to close to clip holding position when the clip holding tool is drawn into the tubular clip opening fitting, and means on the tubular clip opening fitting engageable with the aneurysm clip for causing opening of the aneurysm clip as the clip holding tool is advanced along the tubular clip opening fitting.

4. A holder as in claim 3 which includes a stop member bearable on the first handle means and on the second handle means to limit advance of the handle means under urging of the spring means.

5. A holder as in claim 3 wherein the rod means is rotatably mounted in the first handle means and in the second handle means and rotation of the rod mean causes rotation of the aneurysm clip.

* * * * *